United States Patent [19]
Ito et al.

[11] Patent Number: 6,043,046
[45] Date of Patent: Mar. 28, 2000

[54] METHOD FOR DETECTION OF ATOPIC DERMATITIS

[75] Inventors: Makoto Ito; Nozomu Okino, both of Fukuoka, Japan

[73] Assignee: Takara Shuzo Co., Ltd., Kyoto-fu, Japan

[21] Appl. No.: 09/120,375

[22] Filed: Jul. 22, 1998

[30] Foreign Application Priority Data

Jul. 22, 1997 [JP] Japan ................................. 9-210190

[51] Int. Cl.$^7$ ............................. C12Q 1/44; G01N 33/92
[52] U.S. Cl. .................................... 435/19; 436/71; 554/1
[58] Field of Search .............................. 435/19, 29, 196; 436/71, 172, 804; 554/1; 514/856

[56] References Cited

U.S. PATENT DOCUMENTS 5,149,794  9/1992  Yatvin et al. ............................. 536/29
5,476,661  12/1995  Pillai et al. ............................. 424/401

OTHER PUBLICATIONS

Raza Aly, Ph.D. et al., "Microbial Flora of Atopic Dermatitis", *Arch Dermatol*, vol. 113, pp. 780–782, Jun. 1977.

J.P. McFadden et al., *British Journal of Dermatology*, vol. 128, pp. 631–632, 1993. No month found.

Donald Y.M. Leung et al., "Immunoglobulin E Antitoxins in Atopic Dermatitis", *Journal of Clinical Investigation*, vol. 92, pp. 1374–1380, Sep. 1993.

B. Melnik et al., *Dermatological Research*, vol. 282, pp. 549–551, 1990. No month found.

A. Yamamoto et al., *Dermatological Research*, vol. 283, pp. 219–223, 1991, No month found.

Genji Imokawa et al., *The Journal of Investigative Dermatology*, vol. 96, No. 4, pp. 523–526, Apr. 1991.

Kumi Jin et al., *Acta Derm Venereol (Stockh)*, vol. 74, pp. 337–340, 1994. No month found.

Susumu Mitsutake et al., *Analytical Biochemistry*, vol. 247, Aritcle No. AB972022, pp. 52–57, 1997. No month found.

*Primary Examiner*—Ralph Gitomer
*Assistant Examiner*—Marjorie A. Moran
*Attorney, Agent, or Firm*—Birch, Stewart, Kolasch, & Birch, LLP

[57] ABSTRACT

The present invention relates to a method for detection of atopic dermatitis, and to a kit for use in the detection of atopic dermatitis. The present invention is useful in cases where it is difficult or almost impossible to distinguish atopic dermatitis from other allergoses when detected by the conventional methods, or where it is difficult to macroscopically distinguish atopic dermatitis from other dermatopathies. Moreover, the detection method of the present invention is also useful as a method of primary screening for atopic dermatitis.

7 Claims, 1 Drawing Sheet

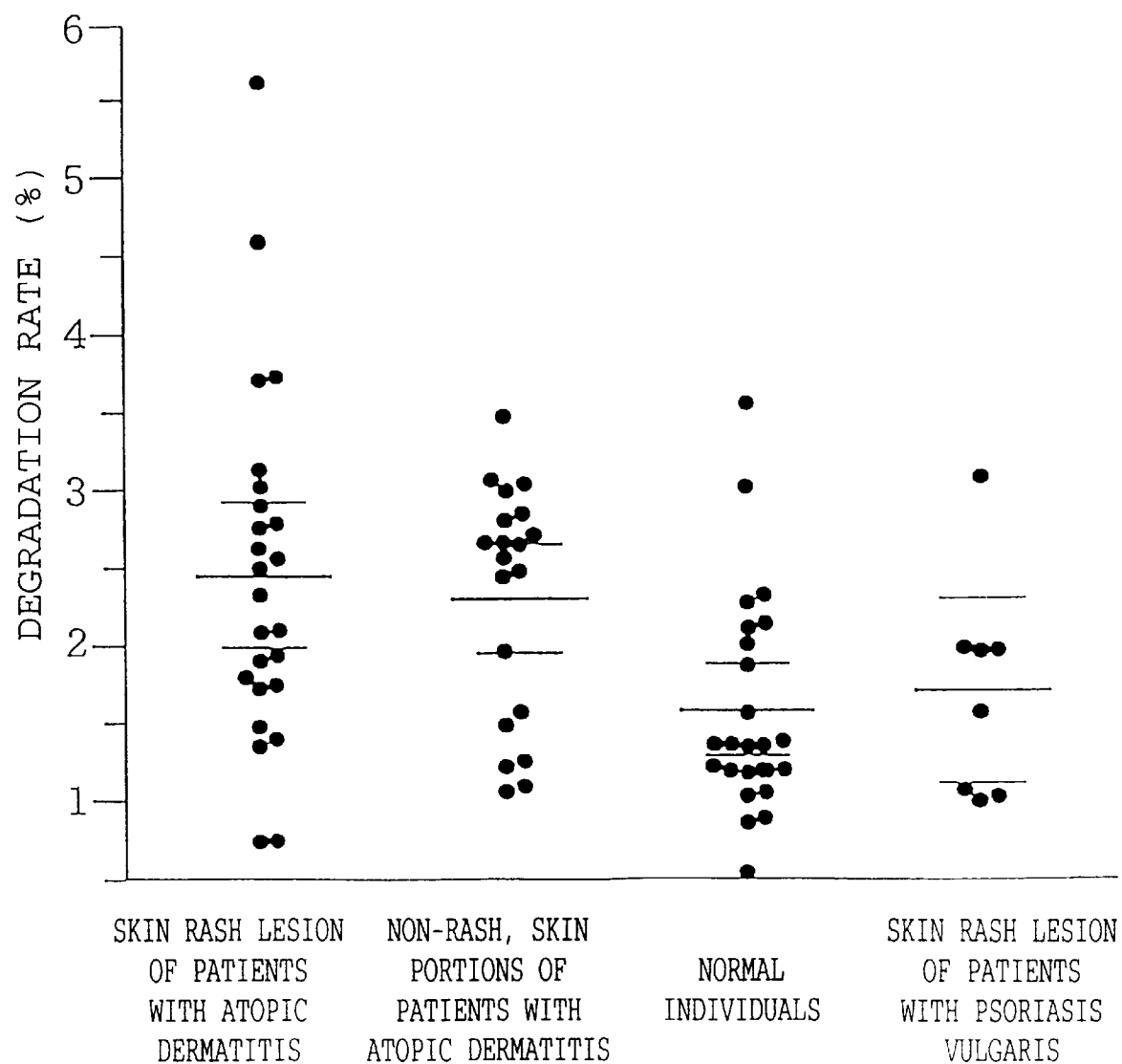
F I G. 1

METHOD FOR DETECTION OF ATOPIC DERMATITIS

BACKGROUND OF THE INVENTION

1. Field of the Invention

The present invention relates to a simple method for detection of atopic dermatitis, and to a kit for use in the method.

2. Discussion of the Related Art

Conventionally, atopic dermatitis has been diagnosed macroscopically or through detailed questioning on mainly clinical symptoms, such as morphologic features and distribution of skin rash, because there have been reported no detection methods for this disease. Clinical examination results are only used for references. For example, serum IgE levels are measured in clinical examination, a high IgE level providing a basis for the diagnosis of atopic dermatitis. It should be noted, however, that elevated IgE levels are observed not only in atopic dermatitis but also in other diseases including allergoses, such as bronchial asthma and allergic rhinitis; parasitic diseases; liver diseases, such as hepatitis, cirrhosis and primary hepatoma; and autoimmune diseases, such as systemic lupus erythematosus. Therefore, a high IgE value is not always directly associated with atopic dermatitis. On the contrary, there has been reported that a significant ratio of patients with atopic dermatitis have perfectly normal serum IgE levels.

Other methods of clinical examination include allergen detection tests, such as peripheral blood eosinophilic leukocyte counting, RAST method (antigen-specific IgE quantitation), scratch test, prick test, and patch test, none of which are necessarily specific to atopic dermatitis.

The above-mentioned methods of clinical examination are all based on the allergic aspects of atopic dermatitis. It is considered, however, that not only allergic aspects but also non-allergic aspects are important in atopic dermatitis.

The non-allergic aspects involve skin dysfunction. Hypofunction is observed in the skin, as a barrier separating the body from the outer environment, of patients with atopic dermatitis.

The ceramide, which accounts for about 50% of the intercorneocyte lipids in the corneal layer of skin, has been considered to protect the skin against drying and to play a key role in the barrier function. To date, a decrease in the ceramide contents has been observed in the skin of patients with atopic dermatitis, suggesting that this change may cause the tendency toward dry skin and a decrease in the barrier function. However, it has not been known why the ceramide contents decrease in the skin of patients with atopic dermatitis.

Also, there have been reported a decrease in the barrier function, and additionally an increase in the microbial cell counts in the skin of patients with atopic dermatitis, with reportedly an increase in the cell counts of various microorganisms, especially *Staphylococcus aureus* and Malassezia fungi. However, these microorganisms are commonly present on the skin, and no differences in the microbial properties have yet been demonstrated between microorganisms from normal individuals and from patients with atopic dermatitis, except for the increase in the cell counts. Also, with regard to microorganisms other than the major microorganisms *Staphylococcus aureus* and Malassezia fungi, no relationships to patients with atopic dermatitis have been demonstrated. No examination methods for atopic dermatitis based on such microbiological viewpoint have been available to date.

As described above, an examination method based on non-allergic aspects, i.e., viewpoints of microbiology and dermatopathy, would be very useful as a supplementary tool for the diagnosis of atopic dermatitis by the conventional examination method based on macroscopic observation or results of detailed questioning and allergic aspects, or as a method of primary screening for atopic dermatitis.

Accordingly, an object of the present invention is to provide a convenient method for detection of atopic dermatitis using samples from the skin.

Another object of the present invention is to provide a kit for use in the above method.

These and other objects of the present invention will be apparent from the following description.

SUMMARY OF THE INVENTION

The present inventors have made intensive studies on microorganisms which are present on the skin of patients with atopic dermatitis, and found that the microorganisms which are present on the skin of patients with atopic dermatitis have a higher ability of producing ceramidase than those from normal individuals. An increase in levels of ceramidase (acylsphingosine deacylase: EC 3.5.1.23) is likely to cause a decrease in the ceramide contents, and can be assumed to involve exacerbation of atopic dermatitis. The ceramide is hydrolyzed by the action of ceramidase to the sphingosine base and fatty acids. The sphingosine, a hydrolyzate resulting from ceramide hydrolysis by ceramidase, is known to suppress the proliferation of skin cells and activate the induction of differentiation. In this point, ceramidase can be assumed to involve exacerbation of atopic dermatitis. The present inventors have found that the levels of ceramidase activities can be used as an index for detection of atopic dermatitis. The present inventors have developed the present invention based on these findings.

In sum, a first embodiment of the present invention pertains to a method for detection of atopic dermatitis comprising measuring ceramidase activity of a sample obtained from a skin of individuals to be tested, and comparing the resulting ceramidase activities with ceramidase activities of a sample obtained from a skin of normal individuals.

A second embodiment of the present invention pertains to a kit for use in the method for detection of atopic dermatitis, comprising a substrate for measuring ceramidase activity.

BRIEF DESCRIPTION OF THE DRAWING

The present invention will become more fully understood from the detailed description given hereinbelow and the accompanying drawing which is given by way of illustration only, and thus, is not limitative of the present invention, and wherein:

FIG. 1 is a graph showing the ceramidase activities in samples from skin surfaces for each individual as measured by the method of the present invention.

DETAILED DESCRIPTION OF THE INVENTION

The present invention will be hereinafter described in detail.

In the present invention, a sample obtained from the skin is not particularly limited. For instance, the obtained samples include desquamation samples from the skin of individuals to be tested, samples obtained by wiping the skin with a tool for collecting samples, such as cotton swab or gauze, and solution samples obtained by washing the skin.

In the present invention, the collection method for skin samples is not particularly limited. Examples of such collection methods include a method comprising collecting a desquamation sample from the skin of individuals to be tested; a method comprising wiping the skin of individuals to be tested with a cotton swab or gauze; and a method comprising bringing a washing solution, such as physiological salt solution or a phosphate buffer, in a cylinder of an appropriate size in close contact with the skin surface, washing the skin surface therewith, and collecting the washings.

The method for measuring the ceramidase activity in a sample from the skin is not particularly limited, as long as the ceramidase activity can be measured at high sensitivity. In order to increase the sensitivity for measuring the ceramidase activity, the microorganisms in the sample may be cultured using an appropriate medium. For this cultivation, any medium can be used, as long as it allows the microorganism in the sample from the skin to grow, and as long as it has a composition which provides efficient ceramidase productivity. Examples of carbon or nitrogen sources include glycerol, glucose, sucrose, molasses, yeast extracts, peptone, corn steep liquor, meat extracts, delipidated soybean, ammonium sulfate, ammonium nitrate, and the like. Besides the above, inorganic substances and metal salts, such as sodium salts, potassium salts, phosphates, magnesium salts and zinc salts, may also be added. Also, a lipid, including sphingomyelin, ceramide, or the like or a surfactant, including taurodeoxycholate, or the like may be added to the medium within the range from 0.001 to 1% by weight to increase the ceramidase productivity, which in turn increase the detection sensitivity.

The culturing conditions for these microorganisms are not particularly limited, and it is desired that the microorganisms are cultured at 25° to 37° C. for 1 to 7 days. By culturing under the conditions, the microorganisms grow to produce the ceramidase. After termination of the culture, the ceramidase activity can be measured by the method described below, using the supernatant of the culture obtained by centrifugation and other means as a sample for measurement.

In the present invention, the substrate for measurement of the ceramidase activity may be any substrate and is not particularly limited, as long as it enables measurement of the ceramidase activity with or without a label. Examples thereof include ceramides with or without a label.

In the present invention, the method for measuring the ceramidase activity is not particularly limited. For instance, the ceramidase activity can be measured by a simple method with a non-labeled ceramide or a labeled ceramide as a substrate.

A labeled ceramide can be prepared by introducing a chromophore-forming substance, a fluorescent substance, biotin, a radioisotope, or the like, into a fatty acid moiety or sphingosine moiety of a ceramide. Examples of the fluorescent substance usable for labeling a ceramide include 7-nitrobenz-2-oxa-1,3-diazole (hereinafter referred as "NBD"); fluorescein and derivatives thereof; rhodamine and derivatives thereof; pyrene derivatives; dansyl; coumarin derivatives; umbeliferone derivatives, and the like. A fluorescent-labeled ceramide, which is labeled with a fluorescent substance so as to quench the fluorescent emission by causing the resonance energy transfer, can be also used. In the case of using the above-mentioned fluorescent-labeled ceramide, ceramidase activities can be assayed by measuring the increase of the fluorescence. Examples of such labeled ceramides include those prepared by the method described in "Methods for Production of Sphingolipids and Sphingolipid Derivatives", Japanese Unexamined Patent Publication No. Hei 10-81655, the disclosure of which is incorporated herein by reference, or the method described in "*Analytical Biochemistry,* 247, No. 1, 52–57 (1997)," the disclosure of which is incorporated herein by reference.

When a non-labeled ceramide is used as a substrate, the ceramidase activity can be measured by incubating the non-labeled ceramide with the sample, and subsequently quantifying the amount of the decomposed ceramide, based on the quantification of the amount of a decrease in the ceramide or the amounts of the decomposition products, free fatty acids or free sphingosine, using thin-layer chromatography or high-performance liquid chromatography.

When a labeled ceramide is used as a substrate, the ceramidase activity can be measured by incubating the labeled ceramide with the sample, subsequently separating the decomposition products from the substrate by various chromatographies, and when the fatty acid moiety is labeled, quantifying the amount of a decrease in the labeled ceramide and/or the decomposition products, free labeled fatty acids. When the sphingosine moiety is labeled, the ceramidase activity can be measured by quantifying the amount of a decrease in the labeled ceramide and/or the free labeled sphingosine.

When ceramidase activity of a sample from an individual to be tested is higher than an average level in normal individuals, it indicates that the tested sample would be that of a patient with atopic dermatitis.

In the present invention, a kit for use in the method for detection of atopic dermatitis is not particularly limited. For instance, the kit includes a reaction buffer and a substrate, and optionally a set of a tool for collecting samples and a medium.

EXAMPLES

The present invention will be described in detail by means of the following working examples, without intending to limit the scope or spirit of the present invention thereto.

Example 1

The microbial ceramidase activity for skin surfaces was measured for 25 cases from normal individuals, 20 cases from skin rash lesions of patients with atopic dermatitis, 24 cases from non-rash, skin portions of patients with atopic dermatitis, and 8 cases from skin rash lesions of patients with psoriasis vulgaris.

The test skin area of each individual to be tested was wiped with a sterile cotton swab, and the cotton swab containing skin portions was then placed in 0.5 ml of a medium (0.5% peptone, 0.1% yeast extract, 0.5% sodium chloride, 0.05% sphingomyelin, 0.005% ceramide, 0.05% sodium taurodeoxycholate), and thereafter the culture was allowed to stand at 30° C. for 5 days. After termination of the cultivation, the culture was centrifuged, and the resulting supernatant of the culture was collected to measure ceramidase activity by the method as described below.

Ten microliters of the culture and 10 $\mu$l of a 50 mM acetate buffer (pH 6.0) containing 100 pmol C16-$^{14}$C-ceramide [*Analytical Biochemistry,* 247, 1, 52–57 (1997)] and 0.5% Triton X-100 were reacted at 37° C. for 6 hours, after which 100 $\mu$l of a chloroform/methanol mixture (chloroform:methanol(volume ratio)=2:1) was added to stop the reaction.

The reaction mixture obtained was evaporated to dryness, and the resulting solid was dissolved in 10 μl of a chloroform/methanol mixture (chloroform:methanol (volume ratio)=2:1) to use the resulting solution as a sample.

After separation by thin-layer chromatography (developing solvent: chloroform:methanol:25% by weight aqueous ammonia(volume ratio)=90:20:0.5), the contents of free $^{14}$C fatty acids and remaining C16-$^{14}$C-ceramide were quantified by using "BAS1000 Imaging Analyzer" (manufactured by Fuji Photo Film Co., Ltd.), and the degradation rate was calculated as an index for detection of the ceramidase activity. The results are shown in FIG. 1. FIG. 1 is a plot for each individual for microbial ceramidase activity levels in the samples from the skin of individuals to be tested. The ordinate is C16-$^{14}$C-ceramide degradation rate (%), and the abscissa is each case. In the figure, the bold horizontal bar for each case indicates an average found value for each case, and the thin horizontal bar indicates the 95% confidence interval for the found values for each case.

As shown in FIG. 1, differences were observed in the distribution of the ceramidase activity produced by microorganisms which were present on the skin surfaces in the samples from normal individuals, those from skin rash lesions of patients with atopic dermatitis, those from non-rash, skin portions of patients with atopic dermatitis, and those from skin rash lesions of patients with psoriasis vulgaris. More specifically, higher ceramidase activity levels were obtained in samples from patients with atopic dermatitis, regardless of whether or not the samples were collected from the skin rash lesions or the non-rash, skin portions, as compared to the samples from normal individuals, even though the ceramidase activity produced by microorganisms which were present on the surface of the skin rash lesions of psoriasis, a dermatitis differing from atopic dermatitis, was comparable to that in the normal individuals.

Example 2

Kit Composition

An atopic dermatitis detection kit (for 20 runs) was constructed as shown in Table 1 using a set of a sterile cotton swab, a medium for microorganisms in samples from the skin, and a reaction buffer containing a substrate for measurement of the ceramidase activity. The medium used contained 0.5% peptone, 0.1% yeast extract, 0.5% sodium chloride, 0.05% sphingomyelin, 0.005% ceramide, and 0.05% sodium taurodeoxycholate. A 50 mM acetate buffer (pH 6.0) containing C16-$^{14}$C-ceramide and 0.5% Triton X-100 was used as a reaction buffer containing a substrate for measurement of the ceramidase activity (simply referred to as "reaction buffer" in Table 1).

TABLE 1

| Cotton Swab | 20 |
| Medium | 10 ml |
| Reaction buffer | 200 μl |

Example 3

Twenty microliters of a mixture [25 mM Tris-HCl buffer (pH 8.5), 2.5 mM calcium chloride and 0.25% Triton X-100] containing 550 pmol of NBD-labeled ceramide disclosed in Japanese Unexamined Patent Publication No. Hei 10-81655 and an appropriate volume of the samples obtained in Example 1, were subject to reaction by incubating at 37° C. for 20 minutes. The reaction mixture was incubated in boiled water for 5 minutes to stop the reaction. Thereafter, the reaction mixture obtained was evaporated to dryness under the reduced condition, and the resulting solid was dissolved in 10 μl of a chloroform/methanol mixture (chloroform:methanol(v/v)=2:1). The resulting solution was separated by thin-layer chromatography in the same manner as in Example 1. The contents of nondegraded NBD-labeled ceramide and free NBD-labeled fatty acid were quantified by using "CS-9300 Chromatoscanner" (manufactured by SHIMADZU Corporation) at 475 nm for excitation wavelength and at 525 nm for fluorescent wavelength, and the degradation rate of a substrate was calculated as an index for detection of the ceramidase activity. The results in the case of using the NBD-labeled ceramide were correlated to the results in the case of using the $^{14}$C-labeled ceramide as a substrate in Example 1.

As described in detail above, according to the present invention, since it is found that levels of the ceramidase activity in samples from the skin, more specifically the ceramidase activity produced by the microorganisms which are present in samples from the skin, serve as a marker for atopic dermatitis, detection of atopic dermatitis can be achieved in a simple manner.

The present invention provides a detection method differing from conventional detection methods based on allergic aspects, and is useful in cases where it is difficult or almost impossible to distinguish atopic dermatitis from other allergoses when detected by the conventional methods, or where it is difficult to macroscopically distinguish atopic dermatitis from other dermatopathies. Moreover, the detection method of the present invention is also useful as a method of primary screening for atopic dermatitis.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for detection of atopic dermatitis comprising measuring ceramidase activity in a cultured skin sample obtained from skin of an individual to be tested, comparing the resulting ceramidase activity with ceramidase activity of a sample obtained from a cultured skin sample of a normal individual, and correlating ceramidase activity with atopic dermatitis wherein higher ceramidase activity as compared to the activity from the normal individual correlates to atopic dermatitis.

2. The method according to claim 1, wherein said sample is obtained from skin surfaces.

3. The method according to claim 2, wherein said sample comprises microorganisms present on skin surfaces.

4. The method according to claim 3, wherein said cultured samples comprise microorganisms which are subject to culture conditions sufficient for growth prior to measuring ceramidase activity.

5. The method according to claim 1, wherein ceramidase activity is measured by reaction with a substrate, wherein said substrate comprises ceramide with or without a label.

6. The method according to claim 5, wherein said substrate is a radioisotope-labeled ceramide.

7. The method according to claim 5, wherein said substrate is a fluorescent-labeled ceramide.

* * * * *